United States Patent [19]

Kehrbach et al.

[11] Patent Number: 4,558,052

[45] Date of Patent: Dec. 10, 1985

[54] 10-BROMOSANDWICINE, 10-BROMOISOSANDWICINE, PHARMACEUTICAL COMPOSITIONS THEREOF, AND METHODS OF TREATING HEART RHYTHM DISORDERS WITH THEM

[75] Inventors: Wolfgang Kehrbach, Hanover; Joachim Wegener, Algermissen, both of Fed. Rep. of Germany

[73] Assignee: Kali-Chemie Pharma GmbH, Hanover, Fed. Rep. of Germany

[21] Appl. No.: 618,908

[22] Filed: Jun. 8, 1984

Related U.S. Application Data

[63] Continuation-in-part of Ser. No. 396,351, Jul. 8, 1982, which is a continuation of Ser. No. 195,618, Oct. 9, 1980, abandoned.

[30] Foreign Application Priority Data

Oct. 13, 1979 [DE] Fed. Rep. of Germany ....... 2941531

[51] Int. Cl.$^4$ ................. A61K 31/435; C07D 455/00; C07D 471/08
[52] U.S. Cl. .................................. 514/279; 514/281; 514/821; 546/40; 546/43
[58] Field of Search .................... 546/40, 43; 424/256; 514/239, 279, 281, 821

[56] References Cited

FOREIGN PATENT DOCUMENTS

| | | |
|---|---|---|
| 2611162 | 12/1977 | Fed. Rep. of Germany . |
| 2941529 | 4/1981 | Fed. Rep. of Germany ........ 546/40 |
| 2941530 | 4/1981 | Fed. Rep. of Germany ........ 546/40 |
| 2941531 | 4/1981 | Fed. Rep. of Germany ........ 546/40 |

OTHER PUBLICATIONS

Volkner et al., "Uber die Herzwirkung von Ajmalinderivaten bei Kaninchen, . . . ", (1962) and English translation.
Petter et al., "Zur Antifibrillaren Herzwirkung von Ajmalin, . . . ", (1962) and English translation.
Anet, et al., J. Chem. Soc., 1954, pp. 1242-1260 (1954).
Petter, et al., Arch. Exptl. Pathol. Pharmakol., 243, pp. 519-527 (1962).
Bonati, et al., Chemical Abstracts, vol. 88, 23231g (1978).
Siddiqui, et al., Chemical Abstracts, vol. 54, 25588c (1960).
Ahmad, et al., Chemical Abstracts, vol. 79, 53652b (1973).
Robinson, Chemical Abstracts, vol. 50, 13957g (1956).

Primary Examiner—Donald G. Daus
Assistant Examiner—Diana G. Rivers
Attorney, Agent, or Firm—Schwartz, Jeffery, Schwaab, Mack, Blumenthal & Evans

[57] ABSTRACT 10-bromosandwicine and 10-bromoisosandwicine and acid addition salts thereof are disclosed. There novel compounds possess valuable pharmacological properties e.g. heart rhythm regulatory properties. Furthermore they are valuable intermediates for the preparation of 10-brominated $N_b$-quaternary sandwicine derivatives which exhibit heart rhythm regulatory and adrenolytic properties. 10-bromosandwicine is prepared by brominating sandwicine and can subsequently be isomerized into 10-bromoisosandwicine.

5 Claims, No Drawings

10-BROMOSANDWICINE, 10-BROMOISOSANDWICINE, PHARMACEUTICAL COMPOSITIONS THEREOF, AND METHODS OF TREATING HEART RHYTHM DISORDERS WITH THEM

The present application is a continuation in part of application Ser. No. 396,351 filed July 8, 1982 which is a continuation of application Ser. No. 195,618 filed Oct. 9, 1980 now abandoned.

BACKGROUND OF THE INVENTION

The invention relates to 10-bromosandwicine and 10-isobromosandwicine, methods for preparing same and pharmaceutical compositions thereof, and their use as chemical intermediates.

Sandwicine is an indole alkaloid from the group of rauwolfia alkaloids. This alkaloid is described in detail by M. Gorman et al, Tetrahedron 1, (1957) pp. 328–337. It is an isomer of the rauwolfia alkaloid ajmaline. Ajmaline and its isomer isoajmaline have been known to possess cardiac activities including antiarrhythmic activities. 10-bromoajmaline also is known to possess cardiac activities (see Petter et al, Arch. Expt. Pathol. Pharmakol. 243, 519–527 (1962)). However from what is known in the art about the cardiac activities of bromoajmaline it can be concluded that the pharmacological profile of ajmaline and its antiarrhythmic activity were not improved by bromination, yet there is in indication of a tendency towards an increase of harmful side effects (see Voelkner et al Z. ges. exp. Med. 1135, 330–354 (1962)).

Contrary to ajmaline no significant antiarrhythmic activities could be detected for sandwicine and isosandwicine in a standard pharmacological in vivo test procedure.

Quarternary salts of ajmaline and isoajmaline are known to possess valuable pharmaceutical properties in particular antiarrhythmic properties. A well known representative of these known quarternary ajmaline and isoajmaline derivatives is a mixture of $N_b$-propylajmalinum and $N_b$-propylisoajmalinium hydrogentartrate which is the active ingredient of an antiarrhythmic pharmaceutical composition which is commercially available under the tradename Neo-Gilurytmal ® and is used in the treatment of disorders in the coronary and circulatory system, especially heart rhythm disorders.

From German Offenlegungsschrift No. 26 11 162 it is known that $N_b$-quarternary derivatives of sandwicine and isosandwicine exhibit valuable pharmacological properties, in particular heart rhythm regulating properties and are useful in the treatment of disorders in the coronary and circulatory system.

It is known that quarternary derivatives of ajmaline, isoajmaline, sandwicine and isosandwicine in addition to their desirable pharmacological properties also possess some undesirable side effects, e.g. negative inotropic properties and sedative side effects.

SUMMARY OF THE INVENTION

It is an object of the present invention to provide novel pharmacologically active 10-brominated derivatives of sandwicine and isosandwicine which exhibit improved pharmacological properties and in particular possess valuable antiarrhythmic properties and a favorable physiological tolerability.

It is a further object of the present invention to provide pharmaceutical formulations containing such brominated sandwicine and isosandwicine derivatives.

It is still a further object of the present invention to provide novel 10-brominated sandwicine and isosandwicine derivatives which are useful as intermediates for the preparation of novel 10-brominated $N_b$-quarternary derivatives of sandwicine and isosandwicine are further improved.

It is a further object of the present invention to provide processes for preparing such 10-brominated sandwicine and isosandwicine derivatives.

In order to accomplish the foregoing objects according to the present invention there are provided novel compounds of the formula I

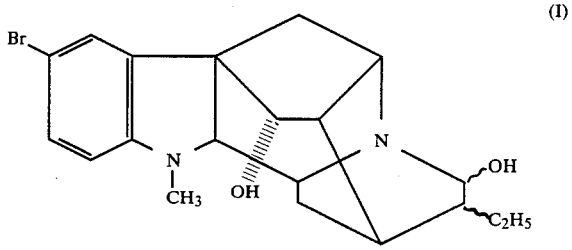

that is 10-bromosandwicine of formula Ia

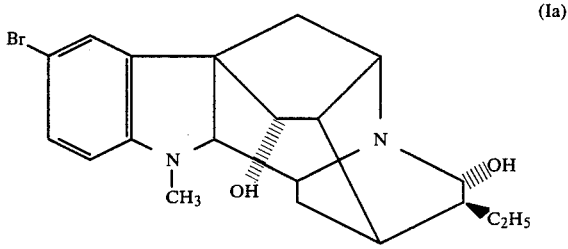

and 10-bromoisosandwicine of the formula Ib

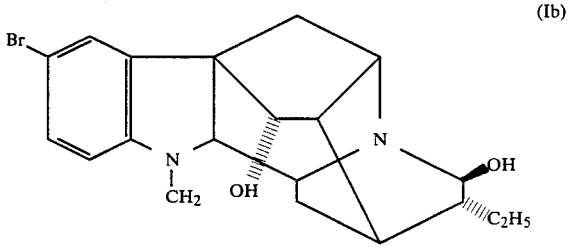

and acid addition salts thereof, in particular acid addition salts with pharmacologically acceptable acids.

The novel compounds of formula I exhibit valuable pharmacological properties, especially antiarrhythmic properties, and are useful in the treatment and prophylaxis of disorders of the coronary system, e.g. of cardiac rhythm disorders.

According to the present invention there are further provided pharmaceutical compositions comprising the above described compounds of formula I and a pharmaceutical carrier.

According to the present invention there is further provided a process for preparing 10-bromosandwicine which comprises brominating sandwicine of the formula II

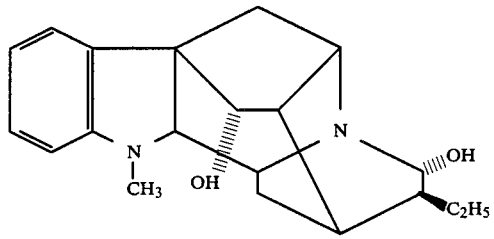

with a brominating agent into 10-bromosandwicine of the formula Ia.

According to the present invention there is further provided a process for preparing 10-bromoisosandwicine of formula Ib which comprises isomerising 10-bromosandwicine.

Further objects, features and advantages of the present invention will become apparent from the detailed description of the invention which follows.

DETAILED DESCRIPTION OF THE INVENTION

The compounds of formula I according to the present invention possess advantageous pharmacological properties, similar to those of the known $N_b$-quarternary ajmaline derivatives. They also are low in side effects and thus exhibit a favourable therapeutic profile and are useful in the treatment and prophylaxis of disorders of the coronary system.

It has been found that compounds with outstanding antiarrhythmic properties and satisfactory physiological tolerability could be obtained by introducing a bromine in 10-position of sandwicine and isosandwicine which themselves show no significant antiarrhythmic effects.

The substantially superior antiarrhythmic activity and therapeutic usefulness of the 10-brominated sandwicine and isosandwicine compounds as compared to the nonbrominated compounds is surprising, since it is known that bromination of ajmaline does not lead to any valuable improvement of its properties.

The superior properties of the brominated compounds of the present invention as compared with the corresponding nonbrominated compounds can be demonstrated by standard pharmacological test methods.

DESCRIPTION OF THE TEST METHODS

A. Determination of acute toxicity $LD_{50}$ i.p. and p.o. in mice.

The acute toxicity of the compounds is determined in male NMRI-mice (body weight range 18–22 g) after i.p. or p.o. administration. The $LD_{50}$ values are calculated by means of electronic data processing through a probit analysis.

B. Determination of minimum symptom dose at which any undesirable side effects are detected.

The minimum symptom dose is determined in male NMRI-mice (body weight range 18–22 g) according to the procedure of Campbell and Richter (see D. E. S. Campbell and W. Richter. Acta Pharmacol. Toxicol. 25 (1967) pp. 345–363). The minimum symptom dose is defined as that dose in μmol/kg which after i.p. administration causes changes in behaviour in 2 out of 3 mice. The minimum symptom dose is a measure for evaluation of undesirable side effects.

C. Determination of antiarrhythmic activity against cardiac extra-systoles induced by aconitine in rats.

The protective effects of the compounds against extra-systoles (ES) caused by aconitine infusion in rats are determined according to the method of Raschack (Arzneimittelforsch. 25 (1975) 639–641).

Male Wistar rats having a body weight of 320–400 g are anesthetized by i.p. application of 1.25 g/kg urethane. The animals are placed on their backs and their electrocardiogram is registered every 30 seconds during the test. The animals are given an i.v. aconitine infusion at an infusion rate of 5 μg/kg/min of aconitine with an infusion volume of 0.1 ml/minute. 5 Minutes prior to starting the aconitine infusion the animals are given a solution of the test compound in an amount of 2 ml/kg bodyweight of isotonic NaCl solution by i.v. infusion over a period of about 2.5 minutes. A control group of animals is given only the vehicle solution. The infusion time until occurence of extra-systoles is determined.

Antiarrhythmically active test compounds lead to a retardation of the onset of aconitine-induced cardiac extra-systoles in the treated animals as compared with the group of control animals. The degree of prolongation of aconitine-infusion time and thus of increase of administered amount of aconitine up to which the animals are protected against the aconitine induced extra-systoles is an indication of the degree of antiarrhythmic activity of the test compounds.

Equitoxic doses of the test compounds are used namely doses which correspond to about 5% of the i.p. $LD_{50}$ of the compound in mice. The % increase in aconitine infusion time (that is % increase of administered amount of aconitine) until onset of the extra-systoles in the treated animals as compared with the control group is determined. The test results are given in table I below.

| Test Compound | Toxicity $LD_{50}$ μmol/kg mice i.p. | Toxicity $LD_{50}$ μmol/kg mice p.o. | Minimum symptom dose i.p. μmol/kg mice | Antiarrhythmic activity ES-inhibiting effect % prolongation of aconitine infusion time until onset of extra-systoles |
|---|---|---|---|---|
| Sandwicine hydrogen tartrate | ~325 | 1530 | 58 | not significant |
| 10-bromosandwicine hydrogen tartrate | 307 | 2200 | 92 | 25 |
| Isosandwicine hydrogen fumarate | ~56 | 471 | 10 | not significant |
| 10-bromoisosandwicine hydrogen tartrate | 25 | 65 | 3 | 25 |

Furthermore it has now been found that the pharmacological properties of $N_b$-quarternary derivatives of sandwicine and isosandwicine can be further improved by introducing a bromine atom in 10-position of the sandwicine structure or the isosandwicine structure respectively. In particular it has been found that 10-brominated $N_b$-quarternary derivatives of sandwicine and isosandwicine exhibit improved adrenolytic and heart rhythm regulating, in particular antiarrhythmic properties as compared with the known commercially available $N_b$-quarternary ajmaline derivatives and at the same time possess lesser side effects. Accordingly these $N_b$-quarternary 10-brominated derivatives of sandwicine and isosandwicine are useful in the treatment of heart rhythm disorders.

The 10-bromosandwicine and 10-bromoisosandwicine according to the present invention are valuable intermediates for the preparation of 10-brominated $N_b$-quarternary sandwicine and isosandwicine derivatives. Valuable pharmaceuticals, e.g. 10-brominated $N_b$-quarternary sandwicine and isosandwicine derivatives can be prepared by quarternizing a compound of formula I in the $N_b$-position. The quarternization of a compound of formula I can be effected by reacting the compound of formula I with a suitable quarternizing agent, e.g., an alkylating agent under conventional quarternizing conditions. Suitable alkylating agents include alkyl halogenides and reactive esters of alkyl alcohols wherein the alkyl group may contain up to 10 carbon atoms. The quarternization can be performed in any conventional manner, suitably by reacting about equimolar amounts of the compound of formula I and the alkylating agent in the presence of an organic solvent at elevated temperatures, preferably reflux temperature. An excess of alkylating agent may serve as at least part of the solvent.

Furthermore the present invention provides pharmaceutical compositions which are useful for medical treatment, in particular for treatment and prophylaxis of dieseases of the coronary and circulatory system, and which comprise an effective amount of 10-bromosandwicine and/or 10-bromoisosandwicine and/or pharmacologically acceptable acid addition salts thereof as the active ingredient. Furthermore there is provided a method for treating heart disorders which comprises administering to a patient in need of such treatment af effective amount of said pharmaceutical composition.

Pharmaceutical compositions containing 10-bromosandwicine, 10-bromoisosandwicine and/or a pharmacologically acceptable acid addition salt thereof may take the form of solid of liquid formulations for enteral, preferably oral, or for parenteral administration. Thus, the formulations may be in the form of capsules, tablets, coated tablets, suppositories, emulsions or solutions. These formulations may comprise conventional pharmaceutical carriers, e.g., solids, such as starch, lactose, mannitol, polyvinyl pyrrolidone or liquids such as sterile water, pharmaceutically acceptable alcohols or fatty oils, and may further comprise pharmaceutical adjuvants, e.g., binders or lubricants for tabletting, stabilizing, flavoring or emulsifying.

The preparation of 10-bromosandwicine comprises bromination of sandwicine with a suitable brominating agent, suitably in the presence of an inert solvent.

Suitable bromination agents include elementary bromine, copper (II)-bromide and 2,4,4,6-tetrabromo-2,5cyclohexadien-1-one, in particular 2,4,4,6-tetrabromo-2,5cyclohexadien-1-one. Suitable solvents include lower alkyl halogenides, e.g. methylene chloride, lower alkyl alcohols, e.g. methanol, dimethyl formamide, tetrahydrofuran and mixtures thereof.

In the bromination with elementary bromine, use of a mixture of methylene chloride and methanol as a solvent and working at a temperature of about 0° C. have been found to be particularly advantageous.

If the bromination is carried out with copper (II)-bromide it is advantageous to use dimethyl formamide as the solvent and to work at about room temperature.

Most advantageous results are obtained when the bromination is carried out with 2,4,4,6-tetrabromo-2,5-cyclohexadien-1-one in a mixture of methylene chloride and tetrahydrofuran under cooling, preferably at a temperature of from about −5° to about −10° C.

10-bromosandwicine can be transformed into 10-bromoisosandwicine by way of isomerization. The isomerization is carried out suitably under alkaline conditions preferably by treating 10-bromosandwicine with an alcoholic alkalihydroxide solution, in particular with methanolic potassium hydroxide solution. Suitably the isomerization is effected at elevated temperature, preferably at the reflux temperature of the solvent.

The invention will now be further described by the examples below:

Examples 1 to 11 pertain to the preparation of 10-bromosandwicine, 10-bromoisosandwicine and acid addition salts thereof.

EXAMPLE 1

10-bromosandwicine hydrobromide 3 grams of sandwicine are dissolved in 50 ml of a mixture of methylene chloride and methanol. A solution of 1.45 grams of bromine in 100 ml of methanol is added very slowly under stirring and cooling in ice. After partial evaporation of the reaction mixture the resulting 10-bromosandwicine hydrobromide is crystallized from acetone.

Yield: 3.4 grams (76%);
Melting point: 210° C., pure n-form.

EXAMPLE 2

10-bromosandwicine 12.4 grams of 10-bromosandwicine hydrobromide are dissolved in 100 ml of methanol under heating. After cooling, diluted sodium carbonate solution is added dropwise until precipitation of 10-bromosandwicine is completed. 10-bromosandwicine is filtered off under suction and is dried.

Yield: 9 grams (87%).
Melting point: 204° C., pure n-form.

EXAMPLE 3

10-bromosandwicine

Diluted sodium carbonate solution is added to 48.2 grams of 10-bromosandwicine hydrobromide and the resulting mixture is extracted 3 times with methylene chloride to which a small amount of methanol had been added. The organic phase is washed with water, dried, and evaporated to dryness.

Yield: 39.6 grams (99%).
Melting point: 204° C., pure n-form.

EXAMPLE 4

10-bromosandwicine 12.5 grams of sandwicine and 19 grams of copper (II)-bromide are dissolved in dimethylformamide and the solution is agitated at room temperature for a period of 4 hours. After distilling off the solvent, the residue is mixed with water, ammonium hydroxide solution is added and the mixture is repeatedly extracted with ethyl acetate. The organic phase is dried, evaporated, the residue dissolved in methanol, and the 10-bromosandwicine is precipitated from the solution by addition of diluted sodium carbonate solution.

Yield: 4.5 grams (29%).
Melting point: 204° C., pure n-form.

EXAMPLE 5

10-bromosandwicine hydrochloride 1 gram of sandwicine and 1.5 grams of copper (II)-bromide are dissolved in dimethylformamide and the solution is agitated at room temperature. After 4 hours, the solvent is distilled off under vacuum, the residue is mixed with water, ammonium hydroxide solution is added and the mixture is repeatedly extracted with ethyl acetate. The organic phase is dried, evaporated, the residue is dissolved in methanol. A methanolic hydrogen chloride solution is added and the mixture is introduced dropwise into ether. The precipitated 10-bromosandwicine hydrochloride is filtered off, washed with ether and dried.

Yield: 0.9 grams (66%).
Melting point: 268° to 270° C., pure n-form.

EXAMPLE 6

10-bromosandwicine 13.2 grams of sandwicine are dissolved in a mixture of 400 ml of tetrahydrofuran, 100 ml of methylene chlorid and a small amount of methanol. At a temperature of −10° C., 16.6 grams of 2,4,4,6-tetrabromo-2,5-cyclohexadien-1-one are added in small portions. After agitating the mixture for 30 minutes at −10° C., the mixture is allowed to slowly warm up to room temperature and then is extracted twice with 2N-sodium hydroxide solution in order to remove the phenol. After washing twice with water the mixture is evaporated, methanol is added and the resulting 10-bromosandwicine is precipitated by means of addition of water.

Yield: 15.1 grams (92%).
Melting point: 204° C., pure n-form.

By acidifying the aqueous phase and extraction with methylene chloride, 2,4,6-tribromophenol can be recovered, which then can be re-used as starting material for the synthesis of 2,4,4,6-tetrabromo-2,5-cyclohexadien-1-one.

EXAMPLE 7

10-bromosandwicine hydrogentartrate 2 grams of 10-bromosandwicine and 0.74 grams of L(+)-tartaric acid are dissolved in a mixture of 20 ml of methanol and 5 ml of methylene chloride, the solution is evaporated to half its volume and the hydrogentartrate is precipitated by dropwise addition of 200 ml of ether.

Yield: 2.4 grams (88%).
Melting point: 208° C., pure n-form.

EXAMPLE 8

10-bromoisosandwicine 15 grams of 10-bromosandwicine and 20 grams of potassium hydroxide are dissolved in 700 ml of methanol and are heated unter reflux for 8 hours. After diluting with 400 ml of water, the mixture is extracted 3 times with methylene chloride, the organic phase is dried, evaporated and the residue recrystallized from methanol.

Yield: 10.5 grams (70%).

Melting point: 173° to 175° C., pure iso-form.

The mixture of 10-bromosandwicine and a small amount of 10-bromoisosandwicine which remains in the mother liquor can again be isomerized.

EXAMPLE 9

10-bromoisosandwicinium hydrogentartrate 2.5 grams of 10-bromoisosandwicine are dissolved in 200 ml of ethyl acetate and a solution of 0.92 grams of L(+)-tartaric acid in 7 ml of acetone is added dropwise. The precipitated hydrogentartrate is filtered off and washed with ethyl acetate.

Yield: 3.1 grams (90%).
Melting point: 210° C., pure iso-form.

EXAMPLE 10

10-bromoisosandwicinium dihydrogencitrate 1 gram of 10-bromoisosandwicine are dissolved in 15 ml of ethyl acetate and a solution of 0.57 grams of citric acid-1-hydrate in a mixture of 3 ml of acetone and 4 ml of ethyl acetate is added dropwise. The precipitated dihydrogencitrate is filtered off under suction, washed with ethyl acetate and dried.

Yield: 1.1 grams (75%).
Melting point: 220° to 222° C., pure iso-form.

EXAMPLE 11

10-bromosandwicine 26.6 grams of sandwicine are dissolved in 2 liters of tetrahydrofuran and methylene chloride (volume to volume ratio of 4:1). 33 grams of 2,4,4,6-tetrabromo-2,5-cyclohexadien-1-one are added in portions at a temperature of −5° C. under agitation. After addition of the last portion, the mixture is further agitated at −5° C. to −10° C. for a period of 30 minutes and then is warmed up to room temperature. Additional methylene chloride is added, the solution is washed twice with 2N-sodium hydroxide solution and subsequently twice with water, the organic phase is evaporated and redissolved in 500 ml of methanol. Water is added slowly and dropwise to the methanolic solution until precipitation of the 10-bromosandwicine is completed. The product is filtered off under suction, washed with water and subsequently with cold acetone and dried.

Yield: 30.1 grams (91%).
Melting point: 204° C., pure n-form.

By acidifying the aqueous alkaline extracts 2,4,6-tribromophenol can be recovered which after recrystallization from petrolether can again be used for the preparation of 2,4,4,6-tetrabromo-2,5-cyclo-hexadien-1-one.

Examples 12 to 14 pertain to alkylation of 10-bromosandwicine and 10-bromoisosandwicine.

EXAMPLE 12a $N_b$-methyl-10-bromosandwicinium iodide

A solution of 12 grams of 10-bromosandwicine and 13 ml of methyliodide in 500 ml of acetonitrile is heated under reflux for 8 hours. The resulting precipitate is filtered off and washed with ethyl acetate.

Yield: 9.5 grams (59%).
Melting point: 240° to 242° C., pure n-form.

EXAMPLE 12b $N_b$-methyl-10-bromosandwicinium hydrogentartrate

Diluted sodium carbonate solution is added to 8.7 grams of $N_b$-methyl-10-bromosandwicinium iodide and the mixture is extracted with ethyl acetate. A solution of 2.4 grams of L(+)-tartaric acid and acetone is added dropwise to the organic phase. The resulting precipitate is filtered off and washed with ethyl acetate.

Yield: 8.0 grams (52%).
Melting point: 166° to 170° C., pure n-form.

EXAMPLE 13a $N_b$-n-propyl-10-bromosandwicinium iodide 10-bromosandwicine is alkylated with n-propyliodide in a method analogous to the method described in Example 12a.

Yield: 67%.
Melting point: 270° C. decomposing, pure n-form.

EXAMPLE 13b $N_b$-n-propyl-10-bromosandwicinium hydrogentartrate

The conversion of $N_b$-n-propyl-10-bromosandwicinium iodide into the hydrogentartrate is carried out in a method analogous to Example 12b.

Yield: 57%.
Melting point: 153 to 155 degrees C., pure n-form.

EXAMPLE 14a $N_b$-n-propyl-10-bromoisosandwicinium iodide

The compound is prepared in a method analogous to Example 12a.

Yield: 87%.
Melting point: 265° C. decomposing, pure iso-form.

EXAMPLE 14b $N_b$-N-propyl-10-bromoisosandwicinium hydrogentartrate 300 ml of diluted sodium carbonate solution are added to 12 grams of $N_b$-n-propyl-10-bromoisosandwicinium iodide. The mixture is extracted 3 times with methylene chloride, the organic phase is dried, largely evaporated and 600 ml of ethyl acetate are added. Into this solution a concentrated solution of 3.1 grams of L(+)-tartaric acid in acetone is added dropwise. The precipitated hydrogen tartrate is filtered off and washed with ethyl acetate.

Yield: 81%.
Melting point: 149 to 151 degrees C., pure iso-form.

What is claimed is:

1. A compound of the formula I (I)

and acid addition salts thereof.

2. The compound as defined in claim 1 which is 10-bromosandwicine of the formula Ia (Ia)

or its acid addition salts with a pharmacologically acceptable acid.

3. The compound as defined in claim 1 which is 10-bromoisosandwicine of the formula Ib (Ib)

or its acid addition salt with a pharmacologically acceptable acid.

4. A pharmaceutical composition comprising an effective amount of 10-bromosandwicine, 10-bromoisosandwicine or pharmacologically acceptable acid addition salts thereof and a pharmaceutical carrier.

5. A method of treating heart rhythm disorders which comprises administering to a patient in need of such treatment an effective amount of a composition as defined in claim 4.

* * * * *